US00PP28054P3

(12) United States Plant Patent
Fonseca

(10) Patent No.: US PP28,054 P3
(45) Date of Patent: May 30, 2017

(54) SHRUB ROSE PLANT NAMED 'MEIZORLAND'

(50) Latin Name: *Rosa hybrida*
Varietal Denomination: Meizorland

(71) Applicant: CP DELAWARE, INC., Wilmington, DE (US)

(72) Inventor: Conception Fonseca, West Grove, PA (US)

(73) Assignee: The Conrad-Pyle Company, West Grove, PA (US)

( * ) Notice: Subject to any disclaimer, the term of this patent is extended or adjusted under 35 U.S.C. 154(b) by 0 days.

(21) Appl. No.: 14/756,361

(22) Filed: Sep. 3, 2015

(65) Prior Publication Data

US 2017/0071084 P1 Mar. 9, 2017

(51) Int. Cl.
*A01H 5/02* (2006.01)

(52) U.S. Cl.
USPC ..... Plt./103

(58) Field of Classification Search
USPC ..... Plt./103
CPC ..... A01H 5/0222
See application file for complete search history.

*Primary Examiner* — Kent L Bell
(74) *Attorney, Agent, or Firm* — Buchanan Ingersoll & Rooney PC

(57) ABSTRACT

A new and distinct shrub rose plant is provided that abundantly and substantially continuously forms in clusters attractive cup-shaped very double white blossoms that clean well upon full maturity. The plant exhibits a vigorous compact and spreading ground cover growth habit. The foliage is medium green with a semi-glossy finish on the upper surface. The white blossom coloration contrasts nicely with the medium green foliage. The disease resistance during observations to date has been observed to be excellent, particularly with respect to black spot, rust, and powdery mildew. The plant is well suited for providing attractive ornamentation in the landscape.

2 Drawing Sheets

Figure 1:
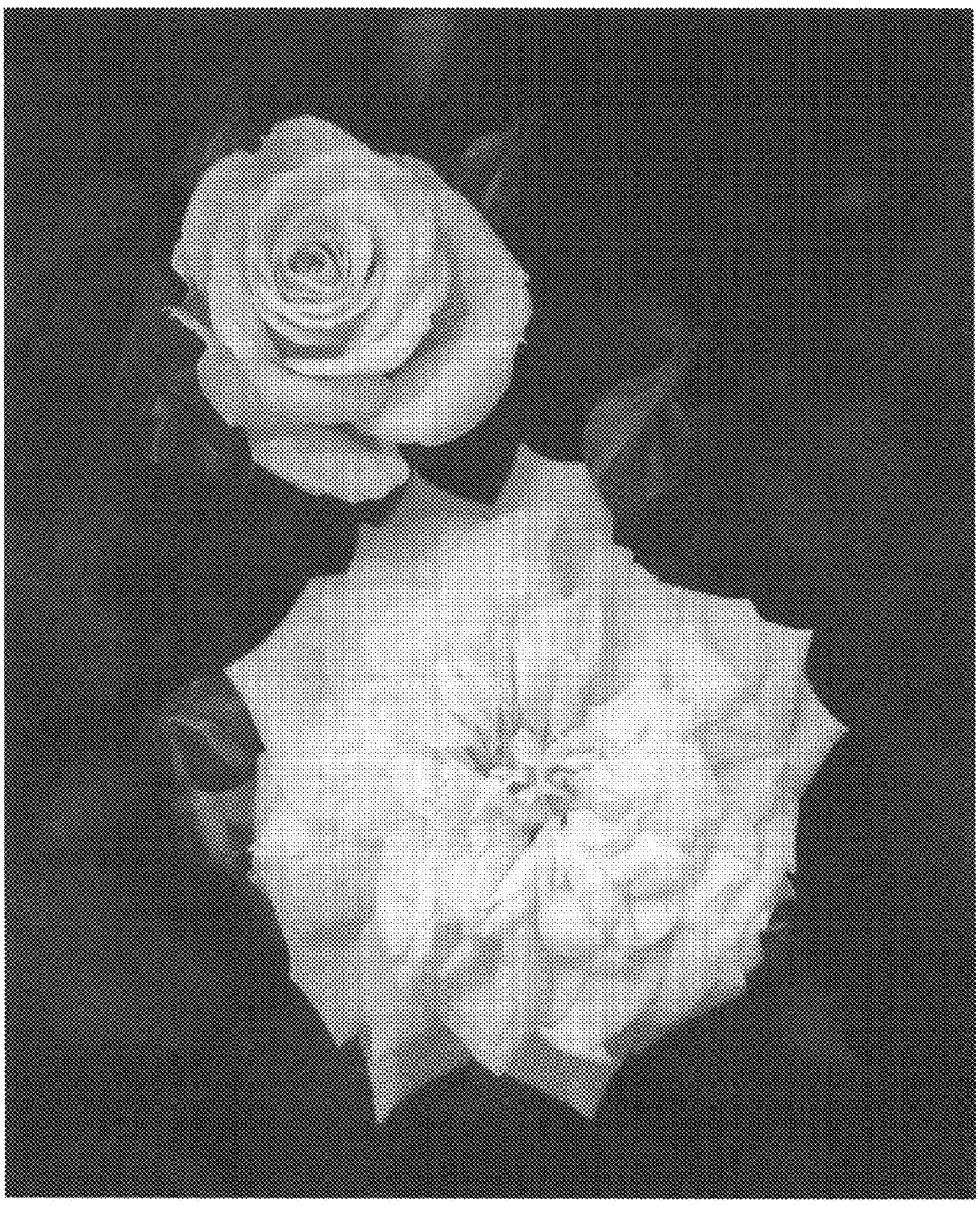

Botanical/commercial classification: *Rosa hybrida*/Shrub Rose Plant.

Varietal denomination: cv. Meizorland.

SUMMARY OF THE INVENTION

The new variety of *Rosa hybrida* shrub rose plant of the present invention was discovered as a branch mutation during 2011 at West Grove, Pa., U.S.A., while growing in a plant nursery setting tended by man among asexually propagated plants of the 'Meiwetdom' variety (U.S. Plant Pat. No. 21,612). The cansation of the mutation is unknown. Had the mutation not been discovered and preserved it would have been lost to mankind.

It was found that the new shrub rose plant of the present invention possesses the following combination of characteristics:

(a) abundantly and substantially continuously forms in clusters attractive cup-shaped very double white blossoms that clean well upon full maturity,
(b) exhibits a vigorous compact and spreading ground cover growth habit,
(c) forms attractive medium green foliage with a semi-glossy finish on the upper surface that contrasts well with the white blossom coloration,
(d) exhibits excellent disease resistance particularly with respect to black spot, rust, and powdery mildew, and
(e) is well suited for growing as attractive ornamentation in the landscape.

A new rose variety is provided having attractive very double white blossoms, a ground cover growth habit, and excellent disease resistance.

The new variety develops well on its own roots following asexual propagation and well meets the needs of the horticultural industry. It can be grown to advantage as an ornamental ground cover in parks, gardens, public areas, and in residential settings. It serves well as a mass planting or can be grown in containers where attractive ornamentation is desired.

The new variety can be readily distinguished from its parent 'Meiswetdom' variety upon an inspection of the blossoms. More specifically, the 'Meiswetdom' variety displays dissimilar blossoms having a medium pink coloration.

The new variety of the present invention also can be readily distinguished from other shrub rose plants including the 'Meigalpio' variety (U.S. Plant Pat. No. 17,877), the 'Meijocos' variety (U.S. Plant Pat. No. 18,874), the 'Meiggili' variety (U.S. Plant Pat. No. 18,542), and the 'Meidrifora' variety (U.S. Plant Pat. No. 19,148). For instance, the 'Meigalpio' variety forms small brilliant red-pink blossoms, the 'Meijocos' variety forms deep pink blossoms with fewer petals, the 'Meiggili' variety forms bright peach blossoms, and the 'Meidrifora' variety forms deep coral-orange blossoms.

The characteristics of the new variety have been found at Wasco, Calif., U.S.A., and at West Grove, Pa., U.S.A., to be homogeneous and stable and to be strictly transmissible from one generation to another by asexual propagation through the rooting of cuttings. Accordingly, the new variety reproduces in a true-to-type manner by such asexual propagation.

The new variety has been named 'Meizorland', and is being marketed under the WHITE DRIFT Trademark.

BRIEF DESCRIPTION OF THE PHOTOGRAPHS

The accompanying photographs show, as nearly true as it is reasonably possible to make the same in color illustrations of this character, flowering specimens of the new variety. The illustrated rose plants of the new variety were approximately two years of age and were observed during September 2013 while growing on their own roots in the ground of Wasco, Calif., U.S.A.

Figure 2:
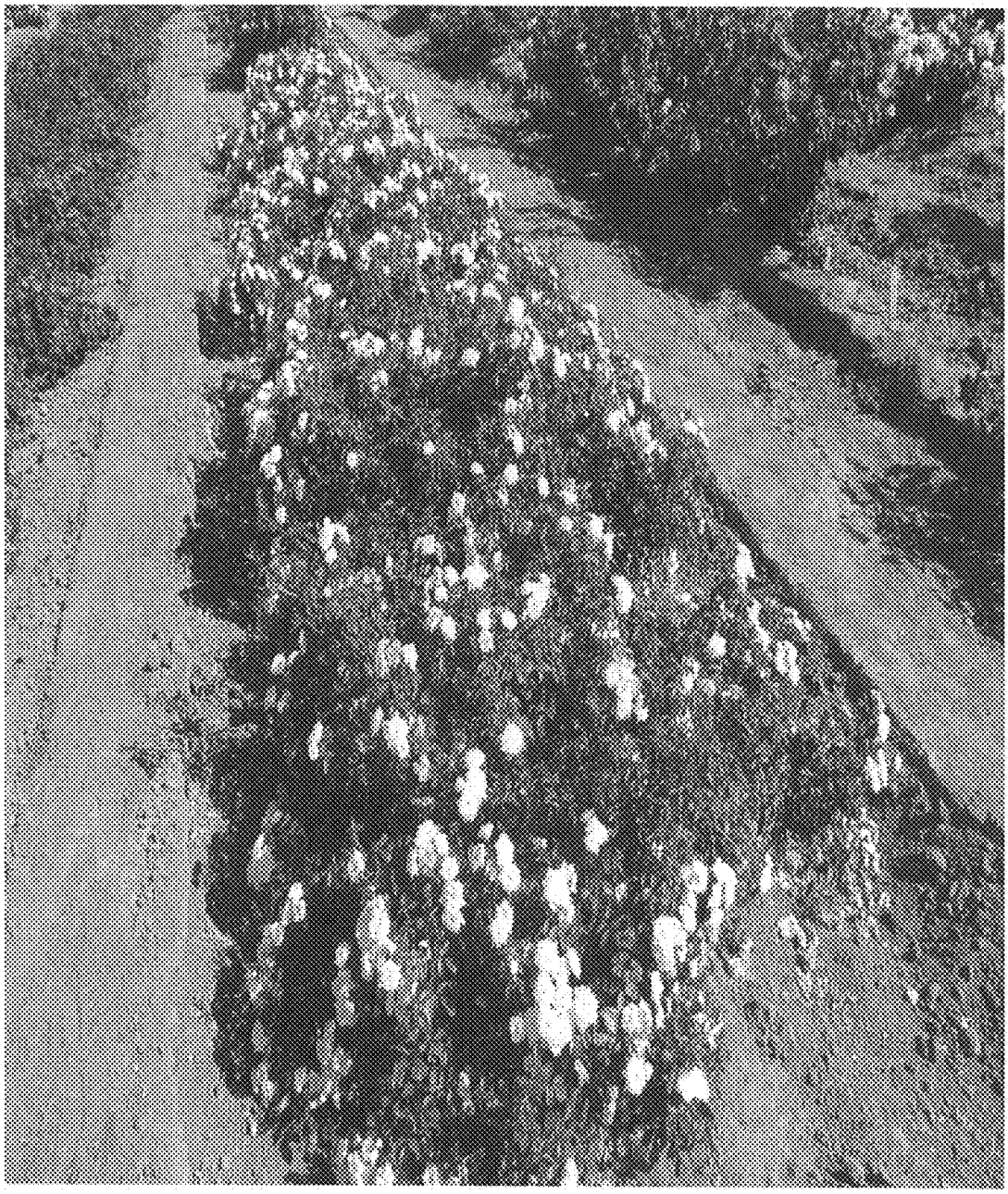

FIG. 1—illustrates a close enlarged view of the attractive cup-shaped double white blossoms with a newly-opened blossom being shown at the top and a mature fully-opened blossom at the bottom, and FIG. 2—illustrates a row of abundantly flowing plants together with nicely contrasting medium green foliage in a plant nursery setting.

DETAILED BOTANICAL DESCRIPTION

The chart used in the identification of colors is that of The Royal Horticultural Society (R.H.S. Colour Chart—1995 Edition or equivalent), London, England. The description is based on the observation of two-year-old specimens of the new variety during May while growing in containers on their own roots at West Grove, Pa., U.S.A.

Class: Landscape Shrub Rose. Variety: 'Meizorland'.

Plant:

*Height*.—Commonly approach approximately 45 cm on average at maturity.

*Width*.—Commonly approach approximately 75 cm on average at maturity.

*Habit*.—Compact and spreading bushy ground cover.

Branches:

*Color*.—Near Green Group 137C on young stems, and commonly near Green Group 137B on old wood.

*Length*.—Commonly main stems approximately 10 cm on average, and secondary stems approximately 17.5 cm on average.

*Diameter*.—Commonly main stems are approximately 1 cm in diameter on average and secondary stems are approximately 7 mm in diameter on average.

*Thorns*.—Size: commonly approximately 9 mm in length on average and approximately 5 mm in width on average at the point of attachment when young, and approximately 7 mm in length on average and approximately 5 mm in width on average at the point of attachment when mature. Quantity and arrangement: commonly approximately 13 thorns on average per stem on immature stems, arranged alternately; commonly approximately 24 thorns on average per stem on mature stems, arranged alternately. Color: commonly near Greyed-Red Group 181B on young stems, and near Brown Group 200B when mature.

Leaves:

*Size*.—Commonly approximately 8 cm in length on average, and approximately 6 cm in width on average for a five-leaflet leaf.

*Leaflets*.—Number 3, 5, 7, and 9. Length: approximately 4 cm on average for a terminal leaflet, and approximately 2 cm on average for a lower leaflet. Width: approximately 2 cm on average for a terminal leaflet, and approximately 1 cm on average for a lower leaflet. Shape: generally ovate in shape, with an acute shape at the apex and a cuneate shape at the base. Margins: serrate. Texture: generally glabrous on the upper surface, and smooth on the under surface. Overall appearance: attractive medium green leaves with a semi-glossy upper surface. Color: (when young): Upper surface: near Yellow-Green Group 144A. Under surface: near Green Group 143C. Color (when fully mature): Upper surface: near Green Group 137A. Under surface: near Green Group 137C.

*Petiole length*.—Commonly approximately 1.5 cm in length on average. Diameter: commonly approximately 1 mm in diameter on average. Color: commonly near Green Group 144C.

*Rachis length*.—Length: Commonly approximately 3.5 cm in length on average. Diameter: commonly approximately 1 mm in diameter on average. Color: commonly near Green Group 144C.

*Stipules*.—Quantity: 2 per petiole. Length: commonly approximately 1.2 cm in length on average. Width: commonly approximately 3 mm in width on average. Shape: generally semi-oval and tapered in shape. Color: commonly near Green Group 144A on the upper surface; commonly near Green Group 144C on the lower surface.

Inflorescence:

*Number of flowers*.—Commonly in clusters of approximately 10 to 15 blossoms per stem, and up to approximately 120 blossoms per plant at a time.

*Peduncle*.—Near Yellow-Green Group 144A in coloration, commonly approximately 3 cm in length on average, approximately 1.5 mm in diameter on average, and smooth with short pubescence.

*Sepals*.—Upper surface: commonly smooth covered with short pubescence, and commonly near Green Group 138B in coloration. Under surface: commonly smooth, and commonly near Yellow-Green Group 144A in coloration. Size: commonly approximately 1.5 cm in length on average, and approximately 5 mm in width at the base. Shape: generally ovate in shape overall with a caudate shape at the apex. Number: five. Margin: entire commonly with extensions on two or three sepals measuring approximately 4 mm in length on average and approximately 0.5 mm in width on average.

*Buds*.—Shape: generally ovoid. Length: approximately 1.2 cm on average as the calyx breaks. Diameter: approximately 7 mm on average as the calyx breaks. Color: near White Group 155A towards the apex and blending to Green-Yellow Group 1D at the base.

*Flower*.—Form: very-double, cuplike. Diameter: commonly approximately 3 cm on average when fully open. Depth: commonly approximately 2 cm on average. Color (when opening begins): Upper surface: near White Group 155A transitioning to near Green-Yellow Group 1D at the point of attachment. Under surface: near White Group 155A transitioning to near Green-Yellow Group 1D at the point of attachment. Color (at end of blooming): Upper surface: near White Group 155B transitioning to White Group 155D at the point of attachment. Under surface: near White Group 155B transitioning to White Group 155A at the point of attachment. Fragrance: none noticeable. Petal number: commonly approximately 80 on average under normal growing conditions. Petal length: commonly approximately 1.8 cm on average. Petal width: commonly approximately 1.2 cm on average. Petal shape: obcordate. Petal margin: entire, and rounded. Petal apex: obcordate. Petal base: rounded. Petal drop: good, the petals commonly detach cleanly and freely drop upon full maturity. Stamen number: approximately 75 on average. Anthers: commonly approximately 3 mm in length and 1 mm in diameter on average and commonly near Yellow-Orange Group 17A in coloration. Filaments: approximately 7 mm in length, and the coloration is near Yellow Group 3A. Pollen: none observed. Pistils: separate and free, and commonly number approximately 20 on average. Styles: commonly approximately 4 mm in length, and near Green-White Group 157B in coloration. Stigma: generally capitate in shape, commonly approximately 5 mm in length and 3 mm in diameter on average, and near Green-Yellow Group 1C in coloration. Receptacle: commonly narrowly ovoid in shape, commonly approximately 4 mm in diameter and approximately 5 mm in depth on average, smooth in texture, near Green Group 139C in coloration, and with achenes commonly being present on the bottom and wall. Hips/seeds: none available for observation.

Development:

*Vegetation*.—Medium green, vigorous, and strong.

*Blossoming*.—Abundant and substantially, continuous from spring to frost.

*Resistance to diseases*.—Excellent, particularly with respect to black spot, rust, and powdery mildew.

Plants of the 'Meizorland' variety have not been observed under all possible environmental conditions to date. Accordingly, it is possible that the phenotypic expression may vary somewhat with changes in light intensity and duration, cultural practices, and other environmental conditions.

I claim:

1. A new and distinct shrub rose plant characterized by the following combination of characteristics:

(a) abundantly and substantially continuously forms in clusters attractive cup-shaped very double white blossoms that clean well upon full maturity, (b) exhibits a vigorous compact and spreading ground cover growth habit, (c) forms attractive medium green foliage with a semi-glossy finish on the upper surface that contrasts well with the white blossom coloration, (d) exhibits excellent disease resistance particularly with respect to black spot, rust, and powdery mildew, and (e) is well suited for growing as attractive ornamentation in the landscape;

substantially as herein shown and described.

* * * * *